United States Patent [19]

Fuesting

[11] 4,448,750

[45] May 15, 1984

[54] STERILIZATION METHOD

[76] Inventor: Michael L. Fuesting, 449 N. First St., Wood River, Ill. 62095

[21] Appl. No.: 495,922

[22] Filed: May 23, 1983

Related U.S. Application Data

[63] Continuation of Ser. No. 271,013, Jun. 5, 1981, abandoned.

[51] Int. Cl.³ .............................. A61L 2/10; A61L 2/18
[52] U.S. Cl. ........................................ 422/20; 422/24; 422/28; 422/36; 422/37; 422/300
[58] Field of Search ...................... 422/20, 24, 28, 186, 422/292, 300, 36, 37; 134/1, 25.4, 85; 250/455.1

[56] References Cited

U.S. PATENT DOCUMENTS

| | | | |
|---|---|---|---|
| 3,007,814 | 11/1961 | Bulat | 134/1 |
| 3,478,758 | 11/1969 | Davies | 422/24 |
| 3,672,823 | 6/1972 | Boucher | 134/1 |
| 3,697,222 | 10/1972 | Sierra | 21/54 A |
| 3,912,450 | 10/1975 | Boucher | 21/54 |
| 3,955,922 | 5/1976 | Moulthrop | 21/102 R |

FOREIGN PATENT DOCUMENTS

| | | | |
|---|---|---|---|
| 2207328 | 8/1973 | Fed. Rep. of Germany | 422/24 |
| 947700 | 1/1964 | United Kingdom | 134/1 |
| 2040150 | 8/1980 | United Kingdom | 422/24 |
| 460081 | 8/1975 | U.S.S.R. | 134/1 |

OTHER PUBLICATIONS

M. L. Fuesting and A. N. Bahn, "Synergistic Bacterial Activity of Ultrasonic, Ultraviolet Light and Hydrogen Peroxide", AADR Abstracts #493, 1980.
Él'piner, Ultrasound, Physical, Chemical and Biological Effects, Consultants Bureau, New York, 1964, pp. 266-289.
Boucher, M. G., Ultrasonics: A Tool To Improve Biocidal Efficacy of Sterilants or Disinfectants in Hospital and Dental Practice, Canadian Journal of Pharmaceutical Sciences, vol. 14, No. 1, 1979, pp. 1-12.
Boucher, M. G., Advances in Sterilization Techniques State of the Art and Recent Breakthroughs, American Journal of Hospital Pharmacy 29, pp. 660-672 (Aug.), 1972.

Primary Examiner—David L. Lacey
Attorney, Agent, or Firm—Christel, Bean & Linihan

[57] ABSTRACT

A method for disinfecting and/or sterilizing small objects such as medical and dental instruments and the like wherein the object to be disinfected and/or sterilized is contacted with a liquid, such as an aqueous solution of sodium dodecyl sulfate and carbamide, which is substantially transparent to ultraviolet radiation and has some bactericidal activity itself, at a temperature in the range from about 0° C. to about 100° C. and preferably at about 25° C., and the object while contacted by the liquid is exposed simultaneously to ultrasonic radiation having a frequency in the range from about 8 kilohertz to about 300 kilohertz, preferably from 15 kilohertz to 60 kilohertz, with an energy density of application from about 10 watts/liter to about 5 watts/milliliter, and to ultraviolet radiation having a wavelength in the range from about 1500 Å to about 4000 Å, preferably at about 2537 Å.

12 Claims, 2 Drawing Figures

STERILIZATION METHOD

This is a continuation of application Ser. No. 271,013, filed June 5, 1981, now abandoned.

BACKGROUND OF THE INVENTION

This invention relates to the art of sterilization and/or disinfection, and more particularly to a new and improved method and apparatus for sterilizing small objects such as medical and dental instruments and the like.

One area of use of the present invention is in sterilizing dental instruments, although the principles of the present invention can be variously applied. A procedure for effective sterilization of a wide assortment of dental instruments is essential in every dental office. This is necessary in order to eliminate the transmission of streptococcal and staphylococcal diseases, syphilis, hepatitis, and tuberculosis caused by improper or faulty sterilization methods. The sterilization procedures in common use heretofore have been effective, but unfortunately tend to be time-consuming and relatively expensive. Pre-scrubbing, packaging, sterilization, exhaust and cool down periods are seldom convenient and require considerable time. Gradual instrument damage from steam, heat or corrosive gases is another disadvantage. Furthermore, an increased use of dental auxiliaries has resulted in a dramatic increase in the number of patients a dentist serves per day. This trend, in many cases, has led to a serious bottleneck at the sterilizer. The dentist is usually confronted with two alternatives: to purchase many additional sets of instruments or to resort to using solutions of chemical disinfectants for short periods of time. The first alternative is expensive and the second alternative is not effective.

Unfortunately, the trend of the past has involved use of short-cut procedures including more disinfecting solutions (90–95% kill) and less sterilization (100% kill). It should be emphasized that the 5 to 10% of the microorganisms not killed by disinfectants tend to be the more pathogenic and most disinfectant resistant of the microbes. As a result, chemical disinfection procedures allow for selective infection of patients by only the strongest and highly resistant strains of microbes. The eventual result of this inherent selective mechanism will show striking similarities to the development of the many penicillin-resistant strains not present before the widespread use of penecillin. The number of microbes with which a patient is inoculated is also a critical factor in the severity of the infectious disease. Any reduction in the number of microbes is a positive action and this is why proper use of disinfectants can be of positive value. The present trend away from sterilization must be reversed in order to maintain a high quality of dental care delivery and prevent needless transmission of diseases.

New and different techniques are needed to break the financial and temporal barriers of sterilization so that it can readily be used by all dentists. The development of such a simplified system would eliminate the temptation to cut corners and would more fully encourage dentists to sterilize their instruments, thereby improving the quality of dental care delivery.

A practical solution to the present problems of dental sterilization is to find a method that would both clean soiled instruments and achieve complete sterilization quickly, be cost effective and yet be gentle to the instruments. Such a method would have the following qualities:

1. Rapid sterilization (10 minutes or less for complete cycle).
2. Eliminate pre-scrubbing of instruments.
3. Leave no residue on the instruments (no rinsing).
4. Operate at ambient temperature to allow for sterilization of certain plastic and other heat sensitive items.
5. Use no harsh chemicals so as not to be corrosive or harmful to the instruments or toxic to the operator.
6. Be more economical with less capital investment and lower operating costs.

Such a method would enable the dentist to clean and sterilize all instruments and not be penalized by the cost of additional instruments or by the loss of precious time. Such a method would provide an end to the inconvenience of the traditional sterilization techniques.

SUMMARY OF THE INVENTION

It is, therefore, a primary object of this invention to provide a new and improved method and apparatus for sterilizing small objects such as medical and dental instruments and the like.

It is a further object of this invention to provide such a method and apparatus which achieves complete sterilization relatively rapidly.

It is a further object of this invention to provide such a method and apparatus which is operable at room temperature.

It is a further object of this invention to provide such a method and apparatus which eliminates pre-scrubbing of objects and leaves no residue on the objects thereby requiring no rinsing.

It is a further object of this invention to provide such a method and apparatus which is not harmful to persons using the same and is not damaging to the objects.

It is a further object of this invention to provide such a method and apparatus which is convenient and economical to use.

The present invention provides a method of disinfecting and/or sterilizing small objects such as medical and dental instruments and the like wherein an object to be sterilized is contacted with a liquid which is substantially transparent to ultraviolet radiation and wherein the object while contacted by the liquid is exposed to ultrasonic and ultraviolet radiation. The liquid is relatively chemically stable under the temperature conditions and under the ultraviolet and ultrasonic radiation conditions employed and preferably has some bactericidal activity by itself. The method is carried out in the temperature range from about 0° C. to about 100° C., preferably at about 25° C. The ultrasonic radiation has a frequency in the range from about 8 kilohertz to about 300 kilohertz, preferably between 15 kilohertz and 60 kilohertz, and it has an energy density of application in the range from about 10 watts/liter to about 5 watts/milliliter. The ultraviolet radiation has a wavelength in the range from about 150 nm to about 400 nm, preferably at about 254 nm. The apparatus includes an ultrasonic bath device for containing the objects to be sterilized and the liquid wherein the source of ultraviolet radiation is carried in, above, or around the apparatus and the ultraviolet radiation is directed toward the liquid.

The foregoing and additional advantages and characterizing features of the present invention will become clearly apparent upon a reading of the ensuing detailed

BRIEF DESCRIPTION OF THE DRAWING FIGURES

FIG. 1 is a perspective view of apparatus for carrying out the method of the present invention, the apparatus being shown with the cover in a closed position; and FIG. 2 is a perspective view similar to FIG. 1 showing the apparatus with the cover in a partially open position.

DETAILED DESCRIPTION OF THE ILLUSTRATED EMBODIMENT

Figure 1:
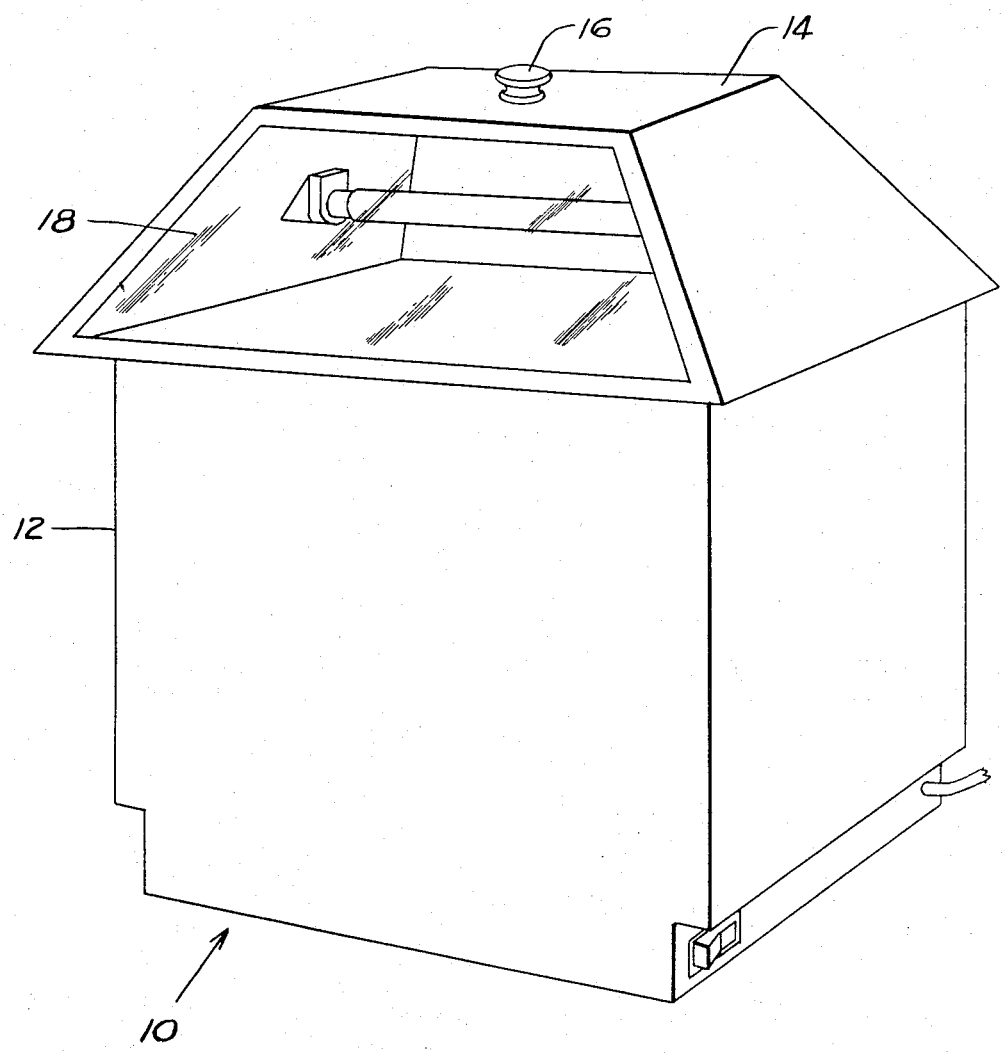

The sterilization method and apparatus of the present invention is a synergistic combination of ultrasonic waves, ultraviolet waves and a liquid solution. By way of background each of the elements of the combination will be considered separately.

With respect to ultrasonic waves, as high frequency sound waves propagate through a liquid, myraids of minute bubbles are generated. The bubbles increase in size until they collapse violently, a condition known as cavitation. The collapse creates forces of a suctioning type that efficiently remove soil, for example saliva, pus, perspriation, organic material and blood found on medical and dental instruments, from any solid surface in the cavitational field. Cavitation also causes denaturation of proteins. Unfortunately, the bacterial cell wall, particularly cocci, usually can resist most cavitational forces. Ultrasonics by itself does reduce microbial populations considerably, but does not achieve sterilization.

The optimal bactericidal effect of ultraviolet radiation occurs around 2600 Å. This is where the ultraviolet maximum absorption occurs in cellular DNA. The radiation acts on nucleic acids to form linkages between thymine bases. The dimers prevent normal base pairing and DNA transcription. Bacteria do have methods of repairing this damage to a small extent, so ultraviolet irradiation is used for very efficient disinfection, but not for sterilization. The pentrability of ultraviolet radiation in water varies inversely with the mineral content of the water. While ultraviolet light can only penetrate 3 to 5 inches into ordinary tap water before 90% of it is absorbed, it is known to penetrate 115 inches into distilled water before the same proportion of it is absorbed.

Surface active agents are compounds known as surfactants and contain both a hydrophobic and hydrophillic portion. They can form a layer that coats and solubilizes portions of membranes causing them to rupture and break. There are many of these surfactants with wide antimicrobial spectrums. They are used in many different applications and are good disinfectants. The major problem with these surfactants is that they do not penetrate bacterial spore coats, or do so very slowly, and are therefore not sporicidal.

As early as 1960, scientists were investigating the germicidal properties of ultrasonic waves. It was found that high intensity ultrasonic waves at short distances could sterilize, however the intensity requirements and distance factor made general sterilization by ultrasonics alone impractical. Ultrasonic cavitation, on the other hand, was found to clean solid surfaces very efficiently, denature proteins, and increase the rates of many chemical reactions. An ultrasonic bath containing water is capable of reducing microbial populations considerably, but does not achieve sterilization.

Over the next ten years, 1965–1975, disinfectant solutions were tested in ultrasonic baths to see if ultrasonic energy would increase their activities. Although many disinfectants were tested and found to be non-sporicidal, Perkulis, Englehardt and Kramer reported in 1970 that benzalkonium chloride, a surface active agent, worked very well on bacteria but this was later also found to be non-sporicidal.

It was reported by Sierra and Boucher in 1971 that the addition of ultrasonic waves to hot acid glutaraldehyde at 60° C. could reduce the sterilization time to just ten minutes. This report proved premature, however, in claiming total sterilization. More rigorous testing with dried spores showed that it took much longer for total sterilization. After several improvements this method has been marketed. It has not, however, replaced the traditional methods of sterilization in the dental/medical fields. This may be attributed to several possible shortcomings. After sonification with glutaraldehyde, instruments must be rinsed with sterile water. This is an inconvenience and recontamination may occur during this process. Glutaraldehyde is very allergenic and the user is advised to wear gloves. Ultrasonic baths can create an aerosol spray and the side effects of a fine aerosol of this toxic and allergenic solution dispersed through out an office are unknown. The elevated temperature (60° C.) required is another inconvenience.

In accordance with the present invention, small objects to be sterilized such as medical and dental instruments and the like are contacted with a liquid which is substantially transparent to ultraviolet radiation and then while the objects are contacted by the liquid they are exposed to ultrasonic radiation the ultraviolet radiation. The foregoing can be carried out in an ultrasonic bath device wherein a source of ultraviolet radiation is carried in the device above the level of the liquid contacting the objects. The temperature of the liquid is in the range from about 0° C. to about 100° C., preferably at about 25° C., although elevated temperatures may enhance the sporicidal activity of the liquid. The ultrasonic radiation has a frequency in the range from about 8 kilohertz to about 300 kilohertz, perferably between 15 kilohertz and 60 kilohertz, and it has an energy density of application to the liquid in the range from about 10 watts/liter to about 5 watts/millileter. The ultraviolet radiation has a wavelength in the range from about 150 nanometers to about 400 nanometers, perferably about 254 nanometers. The effectiveness of the ultraviolet radiation increases as the intensity of its output increases. The liquid is substantially transparent to ultraviolet radiation, is relatively chemically stable under the temperature conditions and under the ultraviolet and ultrasonic radiation conditions employed, and it preferably has some bactericidal activity by itself. The liquid also should facilitate in cleaning, leave no residue and not be irritating, corrosive, allergenic or carcinogenic. Liquids can fulfill some of these requirements including the more important ones, and still provide effective sterilization when used with the method of the present invention. One found to perform satisfactorily is an aqueous solution of sodium dodecyl sulfate (sodium lauryl sulfate) and carbamide (urea) at 1–3% dry weight each. This solution in combination with ultrasonic and ultraviolet radiation according to the present invention has been shown to sterilize in less than three minutes in experiments using AOAC techniques. For a more detailed description of such techniques, reference may be made to Horwitz, W. Official Methods of Analysis of the Association of Official Agriculture Chemists, Washington, D.C., 1965.

Other liquids found to provide satisfying results include aqueous solutions of sodium dodecyl sulfate (sodium lauryl sulfate) alone, aqueous solutions of carbamide (urea) alone, aqueous solutions of surface active quaternary ammonium compounds, distilled water, saline solution, alcohols (isopropyl, ethyl, methyl), polyethylene glycol, organic acids (such as acetic, lauric and myristic), sodium silicate, and sodium bicarbonate. It is believed that the key factor with respect to the liquid is that it has a relatively high transparency in the ultraviolet region of the spectrum. This is to allow the full effects of ultraviolet exposure to any microbes present, without the solution soaking up the ultraviolet light and thus protecting the microbes from the ultraviolet radiation. Transparency also indirectly identifies the solutions that tend to be ultraviolet stable. The energy of ultraviolet light excites and breaks chemical bonds. Thus, if the solution absorbs ultraviolet light it tends to undergo photolytic degradation or other undesirable chemical reactions. The situation in a solution which heavily absorbs ultraviolet light thus can be summarized as follows: the ultraviolet light is destroying the germicial solution, and the solution while absorbing the light would be shading or protecting microbes—a self-defeating system. It can be seen that the ideal solution should absorb little or no ultraviolet light and should have a wide antibacterial spectrum. While some chemicals may be successful in helping to achieve sterilization, many have undesirable properties such as little or no bactericidal activity by themselves, chemical instability under ultraviolet and ultrasonic radiation, corrosiveness and leaving of residue.

In the method of the present invention, the liquid solution is the primary germicide for the vegetative forms present. Its activity is enhanced by the ultrasonic waves which break up any clumps of organisms and expose them to the germicidal liquid. The ultrasonic waves accelerate chemical reactions, denature proteins, and clean even the smallest amount of foreign materials from the instrument or other object being disinfected and/or sterilized. They also mix and churn the surrounding solution, allowing for full exposure to the ultraviolet light. The ultraviolet light damages the DNA of both spores and vegetative forms. The metabolically active vegatative forms can use mechanisms to repair some of this damage, but the liquid kills them by solubilizing their membranes. The bacterial spores, which the surfactants normally cannot penetrate, will have their DNA damaged from the ultraviolet light. Metabolically, bacterial spores are relatively dormant and unable to exercise their repair mechanisms and therefore be deactivated. The select combination of agents according to the present invention offers the possibility for quick, efficient sterilization of dental instruments by means of synergistic interactions.

The present invention is illustrated further by the following examples.

EXAMPLE I

A number of surfactant solutions were tested to determine the general ultraviolet transparency and stability of the solutions. In particular a percent transmittance was determined for each solution at a particular wavelength of ultraviolet light. All chemical solutions unless otherwise noted were of a concentration of 3% by weight using reagent grade chemicals. Other common chemical compounds and germicides were also tested. The data obtained could be used to determine if these compounds could be combined with another solution as an additive to possibly activate, buffer, stabilize or modify in some other desirable manner, the basic solution. In order to assess the ultraviolet absorption of each solution, the ultraviolet spectrum was recorded with a spectrophotometer. The primary wavelength of commercially available germicidal lamps is 2537 Å, so that the percent transmittance at this wavelength was determined for each solution. These values were used to assess the general ultraviolet transparency and stability of the chemical solutions under investigation. The results are presented in Table I which indicates the determined value of percent transmittance to ultraviolet light at a wavelength of 2537 Å. The solvent in the solution was distilled water unless noted by an asterisk which indicates that methanol was used as the solvent. The appropriate solvent was used as the zero and reference for the spectrophotometer to record the ultraviolet data.

TABLE I

| % Transmittance (±0.5%) | Chemical Solution |
| --- | --- |
| 100 | sodium bicarbonate |
| 100 | sodium chloride |
| 100 | urea (carbamide) |
| 97 | sodium dodecyl sulfate |
| 95 | polyethylene glycol |
| 94 | isopropyl alcohol (70%) |
| 94 | ethyl alcohol (100%) |
| 93 | 2-amino-2-(hydroxymethyl)-1,3-propanediol |
| 93 | triethanolamine HCl |
| 92 | myristytrimethylammonium bromide |
| 81 | lauric acid* |
| 79 | myristic acid* |
| 65 | methyl alcohol (70%) |
| 30 | formamide* |
| 24 | benzalkonium chloride(1:1000) |

The following solutions showed a % Transmittance of less than 1.0%.
sodium hypochlorite
liquid phenol*
p-tert-amylphenol*
gluteraldehyde
betadine
hexachlorophene*
hydrogen peroxide
linolenic acid*
0-phenylphenol*
4-n-propylphenol*
resorcinol*
p-chlorophenol*
thiourea

EXAMPLE II

Solutions determined to have a relatively high percent transmittance to ultraviolet light (%T greater than 20%) were employed in the sterilization method of the present invention to determine their effectiveness therein. The test organism used was Bacillus Subtilis (ATCC No. 19659), and the AOAC method previously identified herein was used for growing and harvesting the spores. Approximately 4 ml of a working suspension of the spores (approximately $1 \times 10^7$ spores/ml in Ringers solution) was combined with approximately 36 ml of the liquid surfactant in a sterile 50 ml beaker which, in turn, was suspended in an ultrasonic bath equipped with an ultraviolet light above the bath in a manner which will be described presently. The ultrasonic bath was a Bransonic 52 (Branson-Smith Kline Co. 50/60 Hz, 117 volts, 240 watts) and the ultraviolet lamp employed was a General Electric G2578, 25 watts, germicidal, 60 Hz, 115 volts. The samples were simultaneously exposed to ultrasonic radiation at 52 kilohertz, 240 watts and ultraviolet radiation at 2537 Å wavelength and 300 microwatts/$cm^2$. Samples when there withdrawn after definite intervals, such as 3, 6, 9, 12, 15, 30 and 60 minutes and plated after serial ten-fold dilutions. The cultures were incubated aerobicly at 37° C. for 24 hours before counting. The survival counts for each exposure time to each chemical solution were then plotted on a graph. These deactivation curves showed that most of these chemical solutions were capable of achieving sterilization when used with the method of the present invention, however, some of the solutions were more efficient than others. The more transparent solutions (high %T) tended to be more efficient (quicker sterilization) than those which were less transparent in this test against naked hydrated spores.

EXAMPLE III

In order to better evaluate the solutions in a more realistic situation, the AOAC test utilizing vacuum dried spores on pennycylinders and silk suture loops was used. The conditions used in this test were the same as those in Example II except the 50 ml. beakers contained 40 ml. of the solution being tested and then 5 suture loops or 5 pennycylinders were added, the device was turned on, and then the sutures or pennycylinders were withdrawn and cultured after differing time intervals (i.e. 1, 2, 3, 4, 5, etc. minutes). The above procedure was repeated twenty times for each chemical solution. The other factor in the experimental conditions which was changed from the conditions used in the previous example was that the intensity of the ultraviolet radiation had been increased to 2,000 microwatts/$cm^2$. An aqueous solution of sodium dodecyl sulfate (sodium lauryl sulfate) and carbamide (urea) at 1–3% dry weight each was found to sterilize in less than three minutes using AOAC techniques.

While the above mentioned solution was found to be the most efficient of the solutions tested, a number of other solutions were found to be effective and achieve sterilization when used in the mehod of the present invention. These solutions included sodium dodecyl sulfate (sodium lauryl sulfate) alone in aqueous solution, carbamide (urea) alone in aqueous solution, aqueous solutions of surface active quaternary ammonium compounds, distilled water, saline solution, alcohols (isopropyl, ethyl, methyl), polyethylene glycol, organic acids (acetic, lauric, and myristic), sodium silicate, and sodium bicarbonate. These results indicate that the key factor with respect to the liquid is that it has a relatively high transparency in the ultraviolet region of the spectrum. A second important factor that increases efficiency and reliability of an effective solution is its ability to act as a wetting agent to help reduce surface tension and thus make for more efficient and reliable cleaning action.

Figure 2:
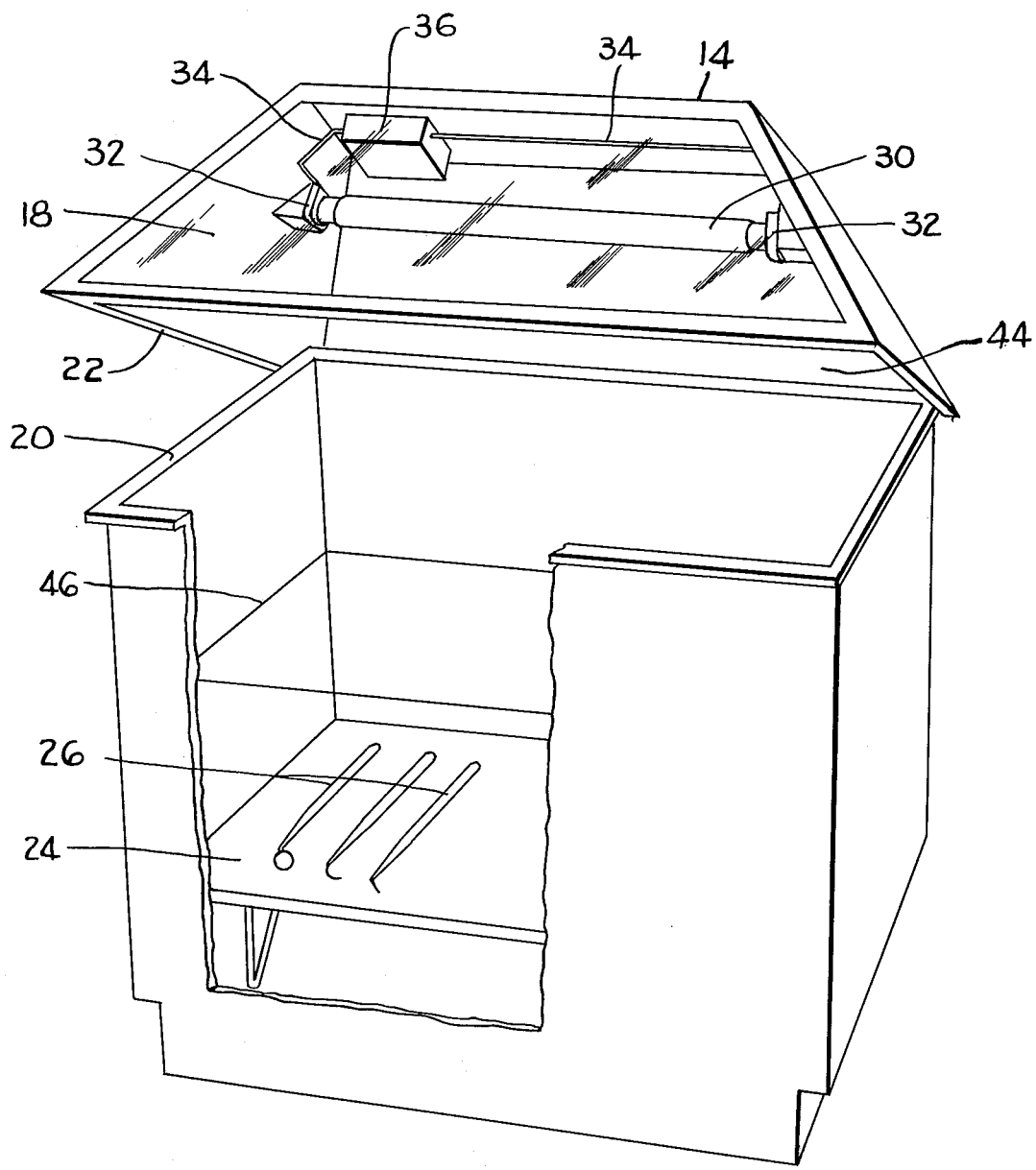

FIGS. 1 and 2 illustrate apparatus according to the present invention for carrying out the method described herein. An ultrasonic bath generally designated 10 has a hollow rectangular body portion 12 with an open top which is closed by a cover or lid 14 hinged to body 12 along one edge in a conventional manner. A handle 16 on lid 14 facilitates manual opening and closing thereof. The front surface of lid 14 is provided with a window 18 of glass which permits viewing of the interior of the apparatus. The glass is of the commonly available window pane type which is known to have a low transmittance to ultraviolet light. The opening in body 12 is bordered by a peripheral flange 20 which cooperates with a lip 22 on cover 14 to prevent escape of ultraviolet radiation from the apparatus interior when cover 14 is closed.

A tray or holder 24 rests within the interior region of body 12 on the bottom surface thereof for holding objects 26 to be sterilized. At least one ultraviolet lamp 30 is provided and electrically connected at opposite ends to a pair of conventional sockets 32 mechanically fixed to opposed inner surfaces of cover 14. Sockets 32 are connected electrically by conductors 34 to a standard ballast transformer component 36 which, in turn, is connected to an electrical supply circuit (not shown) in the ultrasonic bath 10 having appropriate external connection by a conductor and plug to a standard electrical outlet. The supply of electrical power to bath 10 is controlled by a conventional on-off switch.

The ultrasonic bath 10 can be a Bransonic 52—Branson (Smith Kline, 50/60 Hz, 117 volts, 240 watts) with the cover modified to carry ultraviolet lamp 30 which can be a General Electric tube type lamp G2578, 25 watts, germicidal, 60 Hz, 115 volts. The inside of body 12 is of stainless steel or similar metal which is reflective to ultraviolet light. The inside of cover 14 preferably is lined or coated with a layer 44 of ultraviolet light-reflecting material, for example a suitable metal. While one ultraviolet lamp 30 is shown for convenience in illustration, several lamps can be installed in cover 14 in spaced, side-by-side relation. The apparatus can be provided with a safety switch (not shown) electrically in series between lamp 30 and the power supply and operated in response to opening and closing of lid 14 such that the switch is open when the lid is open and closed only when the lid is closed with flange 20 in contact with lip 22.

In operation, tray 24 carrying the objects 26 to be disinfected and/or sterilized, for example medical or dental instruments, are placed in the interior region of apparatus 10 as shown and the liquid is introduced to body 12 to a level 46 covering the objects to be sterilized. Lid 14 is closed and the apparatus then is turned on resulting in simultaneous exposure of the objects 26 to ultrasonic and ultraviolet radiation. The apparatus would be provided with a timer (not shown) to indicate the duration of treatment to the user, and an appropriate timer control could be associated with the power supply to turn the apparatus off after a selected treatment time. Preferably, the safety switch previously described operates to turn off only the ultraviolet lamp if lid 14 is opened to avoid ultraviolet exposure to personnel using the apparatus and still allow the apparatus to operate if only ultrasonic cleaning is desired. The apparatus 10 should be constructed to minimize the required depth of the liquid surfactant in body 12 and also to minimize the distance between ultraviolet lamp 30 and objects 26 when lid 14 is closed.

In some situations, several units of apparatus 10 can be employed, the first bath being used with a cleaning solution to effectively pre-clean the objects before they enter a second bath providing the combination of liquid and ultraviolet and ultrasonic radiation. A third unit could be included to serve as a drying chamber. Transfer of objects from unit to unit could be done manually or in an automated manner. In fields of use where specific objects are to be sterilized, for example a dental instrument tray set up or hospital surgical instruments, the body 12 of the apparatus could be constructed so as to accept a standardized tray which would hold the objects and have a porous bottom to allow for drainage after sterilization. This entire tray then could be carried as an instrument tray or stored in a sterile cabinet until needed. The apparatus can be equipped with a heater and thermometer for operation at higher temperatures if desired.

It is therefore apparent that the present invention accomplishes its intended objects. While an embodiment of the present invention has been described in detail, this is for the purpose of illustration, not limitation.

I claim:

1. A batchwise and static method of disinfecting and/or sterilizing small objects such as medical and dental instruments and the like comprising the steps of:
   (a) contacting an object to be disinfected and/or sterilized with a stationary body of liquid or liquid solution which has a percent transmittance greater than twenty percent to ultraviolet radiation;
   (b) exposing said object while contacted by said liquid to ultrasonic radiation;
   (c) exposing said object while contacted by said liquid to ultraviolet radiation;
   (d) said steps of exposing said object to ultrasonic radiation, ultraviolet radiation and liquid being performed simultaneously; and
   (e) said liquid being relatively chemically stable at the temperature employed and under the ultraviolet and ultrasonic energy conditions employed.

2. The method of claim 1, wherein said ultrasonic radiation has a frequency in the range from about 8 kilohertz to about 300 kilohertz.

3. The method of claim 1, wherein said ultrasonic radiation has a frequency in the range from about 15 kilohertz to about 60 kilohertz.

4. The method of claim 1, when said ultrasonic energy is applied to said liquid at a density in the range from about 10 watts/liter to about 5 watts/milliliter.

5. The method of claim 1, wherein said ultraviolet radiation has a wavelength in the range from about 150 nanometers to about 400 nanometers.

6. The method of claim 1, wherein said ultraviolet radiation has a wavelength of about 254 nanometers.

7. The method of claim 1, wherein said liquid has a temperature in the range from about 0° C. to about 100° C.

8. The method of claim 1, wherein said liquid has a temperature of about 25° C.

9. The method of claim 1, wherein said liquid has bactericidal activity.

10. The method of claim 1, wherein said liquid contains a wetting agent to reduce surface tension and promote cleaning action.

11. The method of claim 1, wherein said liquid is an aqueous solution of sodium dodecyl sulfate and carbamide.

12. A batchwise and static method of disinfecting and/or sterilizing small objects such as medical and dental instruments and the like comprising the steps of:
   (a) contacting an object to be disinfected and/or sterilized with a stationary body of liquid or liquid solution having a temperature in the range from about 0° C. to about 100° C., having a percent transmittance greater than seventy percent to ultraviolet radiation, and having bactericidal activity;
   (b) exposing said object while contacted by said liquid to ultrasonic radiation having a frequency in the range from about 8 kilohertz to about 300 kilohertz and applied to said liquid at a density in the range from about 10 watts/liter to about 5 watts/milliliter;
   (c) exposing said object while contacted by said liquid to ultraviolet radiation having a wavelength in the range from about 150 nanometers to about 400 nanometers;
   (d) said steps of exposing said objects to ultrasonic radiation, ultraviolet radiation and liquid being performed simultaneously; and
   (e) said liquid being relatively chemically stable at the temperature employed and under the ultraviolet and ultrasonic energy conditions employed.

* * * * *